United States Patent [19]

Malinowski et al.

[11] Patent Number: 5,660,180
[45] Date of Patent: *Aug. 26, 1997

[54] INTRAVASCULAR ULTRASOUND IMAGING GUIDEWIRE

[75] Inventors: Igor Malinowski, Harbor City; Robert J. Siegel, Venice, both of Calif.

[73] Assignee: Coraje, Inc., San Francisco, Calif.

[*] Notice: The term of this patent shall not extend beyond the expiration date of Pat. No. 5,520,189.

[21] Appl. No.: 654,416

[22] Filed: May 28, 1996

Related U.S. Application Data

[63] Continuation of Ser. No. 221,261, Mar. 31, 1994, Pat. No. 5,520,189, which is a continuation of Ser. No. 552,430, Jul. 13, 1990, abandoned.

[51] Int. Cl.$^6$ .............................................. A61B 8/12
[52] U.S. Cl. .................. 128/660.03; 128/662.06
[58] Field of Search ................ 128/660.03, 662.06; 604/99–103; 606/159

[56] References Cited

U.S. PATENT DOCUMENTS

| | | | |
|---|---|---|---|
| 4,951,677 | 8/1990 | Crowley et al. | 128/662.06 |
| 5,095,911 | 3/1992 | Pomeranz | 128/662.06 |
| 5,520,189 | 5/1996 | Malinowski et al. | 128/662.06 X |

Primary Examiner—Francis Jaworski
Attorney, Agent, or Firm—Don Halgren

[57] ABSTRACT

An ultrasonic imaging guidewire apparatus for ultrasonic diagnostic imaging of blood vessels, comprising: an elongated, flexible, catheter guide (10) having a plurality of electrical conductors, a transducer seat (11), attached to transducer seat (11) an ultrasonic transducer (14), a flexible distal guidewire (12). Distal guidewire (12) may be ended at its distal end with a protective ball (23). A rotary drive unit (28) for rotation of imaging guidewire together with transducer (14), and an electronic computer (30) for processing signals, obtained by reflecting ultrasonic pulses from tissue of the vessel surrounding transducer (14), into cross-sectional images of vessels.

36 Claims, 3 Drawing Sheets

INTRAVASCULAR ULTRASOUND IMAGING GUIDEWIRE

This is a Continuation application of our U.S. patent application Ser. No. 08/221,261, filed Mar. 31, 1994 and now U.S. Pat. No. 5,520,189, which is a Continuation of our earlier filed application Ser. No. 08/552,430, filed Jul. 13, 1990, (now abandoned) each of which is incorporated herein by reference, in their entirety.

BACKGROUND OF THE INVENTION

This invention relates to guidewires and catheters used for angioplasty and atherectomy, and devices for intraluminal, ultrasound imaging.

DESCRIPTION OF PRIOR ART

U.S. Pat. No. 4,794,931 issued to Yock on Jan. 3, 1989 cites a catheter apparatus, system and method of two-dimensional intraluminal ultrasonography combined with a rotating, cutting tool for atherectomy.

The invention described in this patent cites a catheter for atherectomy having an ultrasonic transducer, mounted on rotating atherectomy cutting tool.

The catheter presented in above the patent, although allowing for radial scanning, does not have the ability to view forward, beyond the distal tip of the catheter.

The rotating cutting tool to which the transducer is attached may subject to cutting forces as the tool cuts into a plaque in a stenosed vessel. Such cutting forces may deflect the tool and the transducer, which are attached to a flexible drive cable. This creates a potential for instability of the axis of rotation of the scanning element and thus affect the stability and quality of the image.

The catheter quoted in the referenced article has a rotating mirror element, which reflects an ultrasound beam from a stationary transducer, deflecting said beam into a direction perpendicular to the axis of the catheter.

This creates the potential for unstable geometry of the ultrasound beam deflection and collection system, and thus for producing an image of poor quality and consistency.

The above mentioned inventions present an interesting embodiment of catheters for intraluminal ultrasound imaging, but nevertheless suffer from a number of disadvantage, such as:

Large size and poor flexibility and thus an inability to access coronary vessels, and to scan in narrowly occluded areas of blood vessels.

Inability to effectively combine the ultrasound imaging and general angioplasty catheter.

Inability to assess the vessel diameter and choose the catheter size, without inserting imaging catheters.

Necessity to insert a catheter for ultrasound imaging and then a second catheter for ultrasound imaging and then a second catheter for angioplasty, which means repeated trauma to the blood vessel.

Inability to center catheter in the vessel if the vessel is larger than the outside diameter of the catheter sheath.

BRIEF SUMMARY OF THE PRESENT INVENTION

The present invention describes an apparatus consisting of a special guidewire, equipped with an ultrasonic transducer, a drive unit, for rotation of guidewire and an electronic computer. The guidewire may be located in a central lumen of an angioplasty catheter.

The electronic computer receives and processes signals from the ultrasonic transducer, mounted on the guidewire, as well as transforms signals received into a video image having diagnostic value to the physician.

The transducer element is attached to an enlarged and flattened part of the guidewire, located near the distal end of guidewire.

When an angioplasty catheter is placed in a vessel over the imaging guidewire, the transducer is located distally in front of a balloon angioplasty catheter. The balloon may be inflated with light pressure to center the angioplasty catheter and imaging guidewire in the vessel, for better imaging.

OBJECTS AND ADVANTAGES

Accordingly besides the objects and advantages of the present invention described above in my patent application, several objects and advantages of the present invention are:

(a) Having a small diameter and therefore the ability to enter coronary vessels and perform ultrasonic scans in the narrowly occluded areas.

(b) Having the ability to inspect occluded areas of blood vessels, prior to insertion of the angioplasty catheter, thus providing information useful in selection of the catheter size.

(c) Having no need for insertion of a special imaging catheter, prior to angioplasty, and thus reduction in patient trauma, and chances of damage to vessel walls.

(d) Having a simple and inexpensive construction of imaging guidewire.

(f) Conforming to a well established standard shape and size of angioplasty guidewires.

(h) Having an ability to be held in a central lumen of angioplasty catheter and held there to be activated at any time during angioplasty procedure.

(i) Having the transducer located forward of the angioplasty balloon thus, in an angioplasty of narrow occlusions, having an ability to scan through occluded areas in front of the catheter and then following it with an angioplasty balloon.

Further objects and advantages of the present invention will become apparent from a study of the drawing figures described in next chapter.

DRAWING FIGURES

In the drawings, similarly related parts have the same number, but a different alphabetic suffix.

Reference Numerals in Drawing Figures

Imaging wire of the present invention may consist of:

| 10 | catheter guide |
|---|---|
| 11 | transducer seat |
| 12 | distal guidewire |
| 13 | manipulating bend |
| 14 | ultrasonic transducer |
| 15 | outside metallization of transducer |
| 16 | internal insulation coat |
| 17 | transducer metallization |
| 18 | metal core of wire |
| 19 | main insulation |
| 20 | outside metallization shield |
| 21 | external protective coat |
| 22 | encoder element |
| 23 | protective ball |
| 24 | proximal end of catheter guide |
| 25 | electrical wires |
| 26 | encoder disk |
| 27 | external protective coat |
| 28 | rotary drive unit |
| 29 | electric motor |
| 30 | electronic computer |
| 31 | angioplasty catheter |
| 32 | exposed shield |
| 33 | rotating mandrel |
| 34 | rotary bearing |
| 35 | cable |
| 36 | housing |
| 37 | slip contacts |
| 38 | rotor winding |
| 39 | stator magnet |
| 40 | switch assembly |
| 41 | return spring |
| 42 | switch contacts |
| 43 | switch cover |
| 44 | inflatable balloon |
| 45 | insulating part |
| 46 | metal contact |
| 47 | mandrel opening |
| 48 | encoder housing |
| 49 | push button |

DESCRIPTION

FIGS. 1 Through 5

Figure 1:
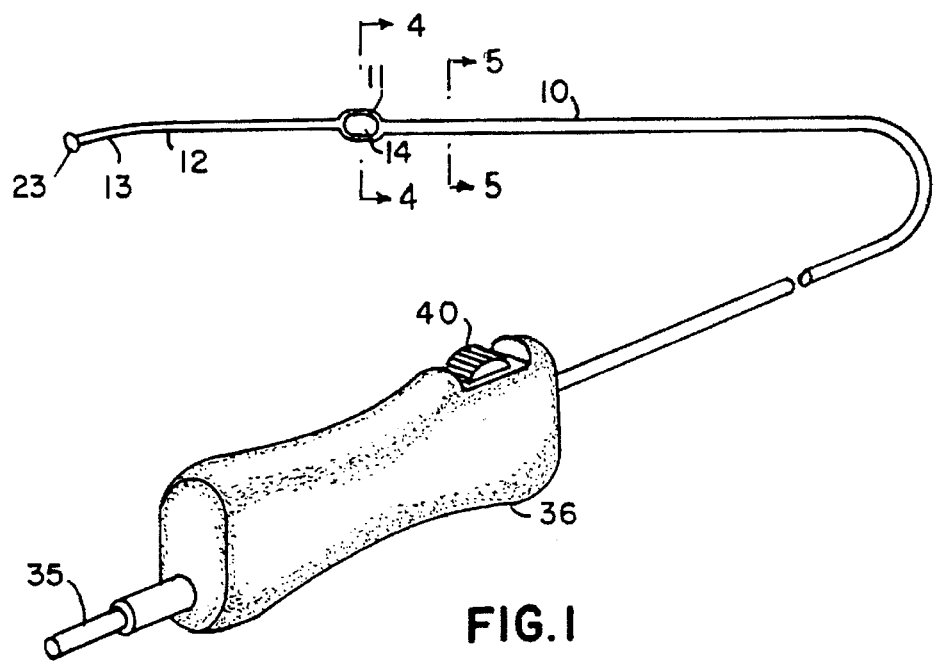
FIG. 1 Shows an overall view of a typical embodiment of the present invention.

FIG. 1 Shows an overall of a typical embodiment of the present invention. Catheter guide 10 part of imaging guidewire is a long stainless steel wire having been coated with multiple layers of insulation and metal, having an outside diameter of approximately 0.018" in diameter, suitable for insertion into the central lumen of an angioplasty catheter. Guide 10 is approximately 39.3 to 78.74 inches (1000 to 2000 mm) long.

Catheter guide 10, at its distal end, is connected with a transducer seat 11, which is flattened and generally wider than the metal core of the rest of imaging wire. Transducer seat 11 may be made of the same metal as guide 10, such as stainless steel 303. Guide 10, transducer seat 11 and distal guidewire may be made of the same piece of metal ground to a desired shape.

Transducer seat 11 is elliptically shaped, 0.050"×0.030" large and approximately 0.015" thick (1.52×0.76×0.38 mm).

An ultrasonic transducer 14 is attached to transducer seat 11 with a this film of electrically conductive epoxy, or other suitable, electrically conductive adhesive.

Ultrasonic transducer 14 is made of a thin, approximately 0.005 inches (0.123 mm) thick disk, of approximately 0.030 inches (0.76 mm) in diameter PZT (lead zirconate-titanate) material such as type EC-66, manufactured by EDO Corporation, Salt Lake City, Utah.

Distal guidewire 12 is connected with seat 11 and is made of stainless steel approx. 0.006" (0.152 mm) in diameter. At the distal end of distal guidewire 12 a manipulating bend 13 may be formed, for easier access to vessel tributaries. Additionally a small protective ball 23 may be formed at the distal end of distal guidewire 13. Protective ball 23 is approximately 0.009 of an inch (0.23 mm) in diameter.

Distal guidewire 12 and ball 23 are coated with a thin (approximately 3–6 micrometers thick) layer of teflon or other suitable, insulating plastic material having a low coefficient of friction.

Catheter guide 10 at a proximal end 21 is connected with a rotary drive unit 28. Drive unit 28 consists of a housing 36 to which a switch assembly 40 and cable 35 are attached. Detailed description of drive unit 28 is provided in connection with FIG. 6.

Figure 2:
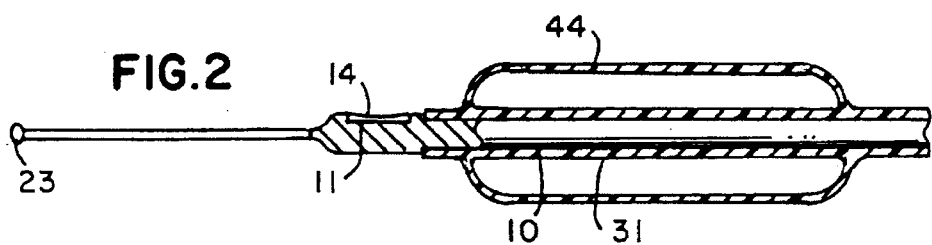
FIG. 2 Show an axial cross section through a typical imaging guidewire of the present invention, inserted into a lumen of an angioplasty catheter, in the plane perpendicular to the surface of an ultrasonic transducer.

FIG. 2 Shows an axial cross section through a typical imaging guidewire of the present invention (See line 2A—2A of FIG. 3) inserted into a lumen of an angioplasty catheter, in the plane perpendicular to the surface of an ultrasonic transducer.

Catheter guide 10 is fitted into a central lumen of angioplasty catheter 31.

Figure 2A:
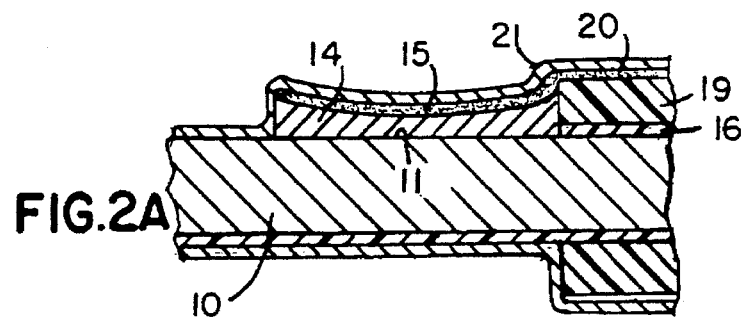
FIG. 2A shows a detailed axial cross sectional view of the transducer taken along the line 2A—2A of FIG. 3.

Transducer seat 11 and transducer 14 are projecting outside angioplasty catheter 31, and are in position for a rotating scan. An inflatable balloon 44 of angioplasty catheter 31 may be inflated with a slight pressure to center the imaging guidewire in the lumen of a blood vessel. Balloon 44 may be inflated with an extensive pressure if angioplasty of vessel walls is desired. FIG. 2A shows a detailed cross sectional view of the transducer 14 of FIG. 2 taken axially, through transducer 14 and transducer seat 11, as well as through metal a metal core 18. Transducer 14 is attached to transducer seat 11 with a film of conductive epoxy or other suitable, conductive adhesive.

Metal core 18, made most suitably of stainless steel (such as type 303), has been coated with a thin (3 micrometers thick) layer of polyethylene, constituting an internal insulation coat 16. Internal insulation coat 16 has been locally removed to permit attachment and electrical contact of transducer 14 with metal core 18.

A main insulation 19 has been applied over the length of catheter guide 10. The thickness of insulation 19 is approximately 120 micrometers or 0.0048 inches. Insulation 19 may be made of homogeneous material such as teflon or polyethylene, or if stiffer catheter guide is required it may be made of polyester resin, reinforced with thin glass or carbon fibers, wound spirally over metal core 18.

Outside metallization shield 20 is a thin layer of aluminum, nickel, silver or other metal, approximately 10 to 20 micrometers thick, deposited over insulation 19. Shield 20 may be deposited using vacuum deposition process.

An outside metallization 15 of transducer connects the upper surface of transducer 14 with outside metallization shield 20 or may be a part of metallization 20.

An external protective coat 21 has been applied over metallization 20. Coat 21 may consist of teflon 3–5 microns thick, vacuum deposited over metallization 20.

Figure 3:
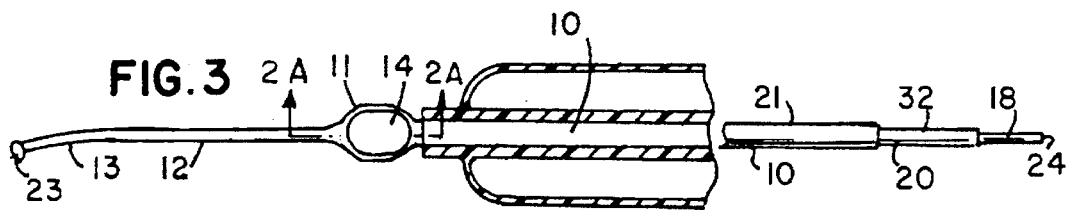
FIG. 3 Shows a partial axial cross section through a typical imaging guidewire of the present invention, inserted into a lumen of an angioplasty catheter, in the plane parallel to the surface of an ultrasound transducer.

FIG. 3 Shows a partial axial cross section through a typical imaging guidewire of the present invention, inserted into lumen of an angioplasty catheter, in the plane parallel to surface of an ultrasonic transducer.

Transducer seat 11 is centered with angioplasty catheter 31 as a result of guide 10 having been inserted into the central lumen of angioplasty catheter 31.

Distal guide wire 12, projecting outside transducer seat 11, may have manipulating bend 13 for easier entry into branches of the blood vessels.

Protective ball 23 may be attached at a distal end of distal guidewire 12.

Near a proximal end 24 of catheter guide 10, external protective coat 21 has been removed, forming an exposed shield 32, which is connected, or may be a part of metallization shield 20.

A part of catheter guide 10, closest to proximal end 24, has its entire coating removed, exposing metal core 18.

Metal core 18 and the exposed shield allow for a convenient electrical connection to transducer 14 from rotary drive unit 28.

Figure 4:
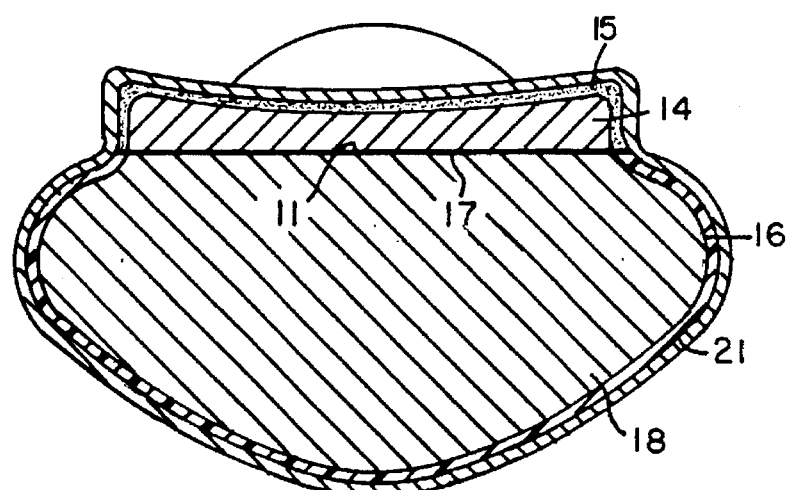
FIG. 4 Shows a cross sectional view, taken along line 4—4 of FIG. 1 of a typical imaging guidewire of the present invention, through ultrasonic transducer, in the plane perpendicular to the axis of an imaging guidewire.
Figure 5:
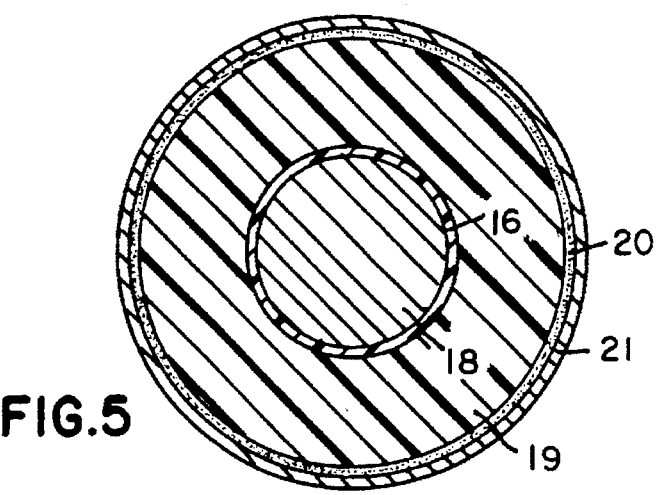
FIG. 5 Shows a cross sectional view of a typical imaging guidewire of the present invention, proximally from an ultrasonic transducer, in the plane perpendicular to the axis of an imaging guidewire.

FIG. 4 Shows a cross sectional view taken along line 4—4 of FIG. 1 of a typical imaging guidewire of the present invention, through an ultrasonic transducer, in a plane perpendicular to the axis of the imaging guidewire and FIG. 5 shows a cross sectional view taken along line 5—5 of FIG 1.

Metal core 18 is larger in this location (having a longer dimension of approximately 0.030 inches or 0.76 mm), slightly elliptical in shape, flattened on top forming transducer seat 11.

Internal insulation coat 16 has been removed in the area of transducer seat 11, to allow electrical contact between core 18 and transducer 14.

Transducer 14 is made of a thin disk of PZT, metallized on its two largest surfaces with a transducer metallization 17, which may be in a form of vacuum deposited gold layer, approximately 1-3 micrometers in thickness.

Transducer 14 is attached to transducer seat 11 through a thin film of electrically conductive epoxy such as Tra-Duct 2924 manufactured by Tra-Con, Inc. Medford, Mass.

Turning now to FIG. 5, insulation 19 has been deposited over coat 16. The thickness of insulation 19 is approximately 120 micrometers or 0.0048 inches.

Insulation 19 may be made of homogenous material such as teflon or polyethylene, or if stiffer catheter guide is required it may be made of polyester resin, reinforced with thin glass or carbon fibers, wound spirally over metal core 18.

Outside metallization shield 20 is a thin layer of aluminum, nickel, silver or other metal, approximately 10 to 20 micrometers thick, deposited over insulation 19. Shield 20 may be deposited using a vacuum deposition process.

Metallization shield 20 is connected with transducer metallization coat 15, and provides an electrical connection to the outside surface of transducer 14 and electrical shielding for the signals transmitted over metal core 18.

Protective coat 21 is applied over the entire surface of the imaging guidewire.

Figure 6:
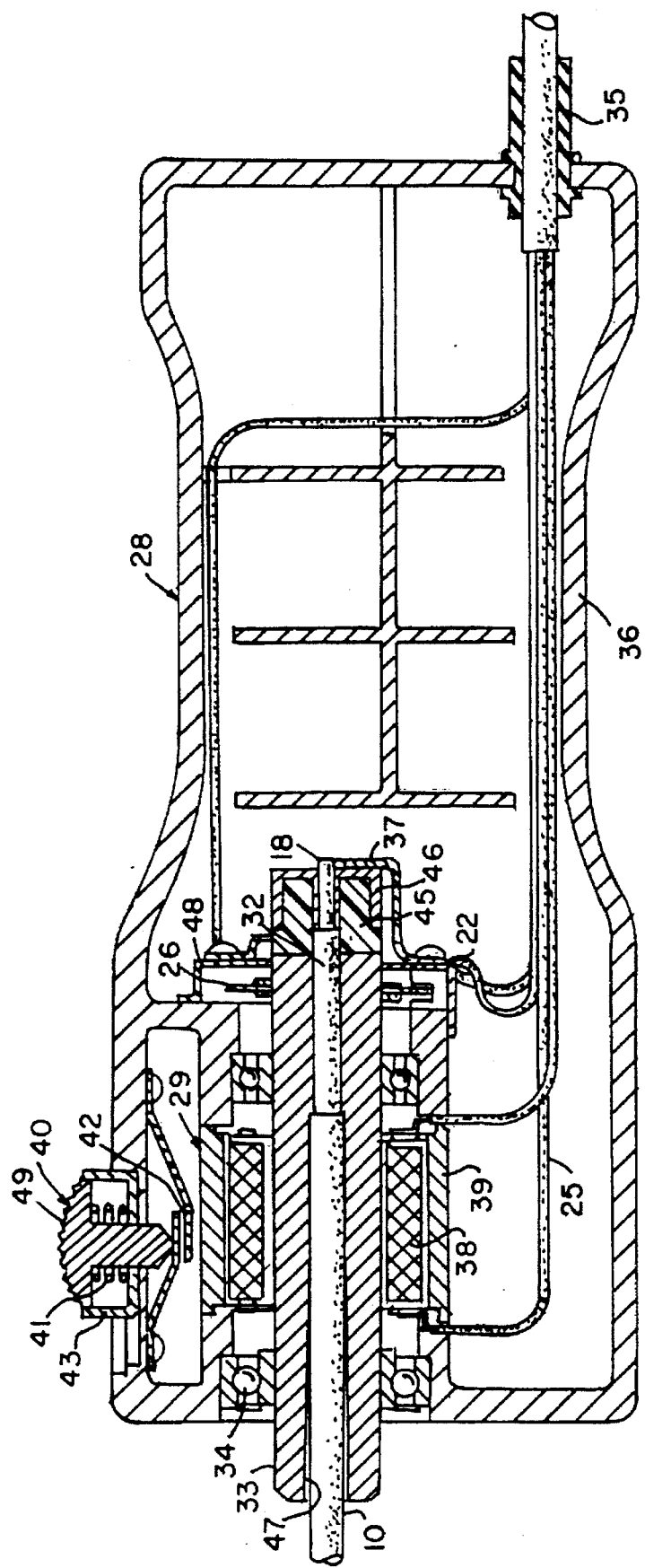
FIG. 6 Shows an axial cross section through a typical rotary drive unit for the imaging guidewire, taken along line 5—5 of FIG. 1 of the present invention.

FIG. 6 Shows an axial cross section through a typical rotary drive unit for imaging guidewire of the present invention.

Rotary drive unit 28 consists of a plastic housing 36, shaped in the form of a compact handle.

A rotating mandrel 33 is rotatably attached in bearings 34, permitting for rotation of mandrel 33. Mandrel 33 is approximately 4 inches (101 mm) long and 0.625 inches (15.8 mm) in diameter. Mandrel 33 has a cylindrical mandrel opening 47, whose dimension resembles the diameter of catheter guide 10. Mandrel opening 47 may be slightly tapered, to allow for locking of catheter guide 10 inside mandrel opening 47.

Mandrel 33 may be made of stainless steel such as the 17-4 type. Electrical connection between exposed shield 32 and stationary slip contacts 37 takes place through mandrel 33.

At its internal end mandrel 33 has an insulation part 45, over which a metal contact 46 has been made. Contact 46 may be made by molding a cylindrical metal part into insulating part 45. The purpose of metal contact 46 is transmission of signals from exposed metal core 18 at the distal end of the catheter guide to slip contacts 37.

Encoder disk 26 is attached to mandrel 33 and has an ability to rotate with mandrel 33. Disk 26 contains marks indicating angular position of mandrel 33. Marks on encoder disk 26 can be read by an optical encoder element 22, which signals to electronic computer 30 angular position of mandrel 33.

Encoder disk 26 and element 22 may be covered by an encoder cover 48 to protect them from contamination.

An electric motor 29 is built into housing 36. Motor 29 consists of rotor windings 38, wound on the rotating mandrel 33 and stator magnet 39, surrounding rotor windings 38.

A switch assembly 40 mounted in the upper area of housing 36 consists of push button 49, retained away from housing 36 by a return spring 41 and a switch cover 43, which is made of flexible plastic material.

Push button 49 may be pressed inside housing 36 or locked in the pushed position by sliding it along the axis of housing 36.

A pair of switch contacts 42 may be closed when pressure of push button 49 deflects once of switch contacts 42 to engage with second one of contacts 42.

Electrical signals to and from slip contact 37, encoder element 22, and electrical power to drive rotor windings 38 through switch contacts 42 is delivered via a set of electrical wires 25.

Electrical wires 25 are routed in a common cable 35 to electronic computer 30 (not shown).

Method of Manufacturing of Imaging Guideware

The imaging guidewire may be manufactured using the following procedure:

The metal core 18 is shaped by grinding. Shaping operation may include shaping catheter guide 10 part, transducer seat 11, distal guidewire 12, protective ball 23.

Next a manipulating bend 12 may be formed.

Guidewire is then subjected to stress relieving which involves heating to and holding at elevated temperatures and controllably cooling. Such treatment is conventionally done to relieve machining stresses in the part.

Next internal insulation coat 16, consisting of a thin coat of polyethylene or parylene (such as parylene C) of approximately 3 micrometers is deposited over the entire surface of imaging guidewire in a vacuum deposition process.

Next coat 16 is locally removed from an area of transducer seat 11 by grinding.

Next transducer 14 is attached to transducer seat 11 via bonding with electrically conductive adhesive.

Transducer 14 may have been previously coated on both larger surfaces with transducer metallization 17, consisting of thinly (approximately 1 micrometer) deposited gold or silver.

The metal is deposited is such a way that the edges and cylindrical surfaces of transducer 14 are free from conductors to prevent a short circuit.

A thick coat of main insulation 19 is applied on the length of catheter guide 10. This may be done in a process of filament winding. In such a process a thin fiber of glass or carbon or other reinforcing material is wetted with polyester resin and spirally wound on core 18 in two directions while, strung between two rotating chucks.

The bending stiffness of the catheter guide may be controlled by varying the pitch of spiral windings of the reinforcing fibers. The fiber is wound back and forth creating a crossing pattern.

Another method, if higher stiffness of the catheter guide is not desired, is to thickly coat catheter guide with approximately 120 micrometers of polyethylene or other suitable plastic, electrical insulator material to form main insulation 19 in a conventional coating process.

Next coats of outside metallization of transducer 15 and outside metallization shield 20 are applied. Both layers of metallization may be applied in the same vacuum deposition process. Distal guideware 12 may be masked off from this operation.

Next a thin layer of teflon is applied on the entire surface of the imaging guidewire to create external protective coat 21. The thickness of this coat may be between 1 and 5 micrometers.

OPERATION

In a typical procedure the physician performing the catherization procedure using the imaging guidewire inserts the guidewire into the blood vessel via an introduction sheath. The guidewire at this point may be already routed through an angioplasty catheter.

Once the guidewire is advanced into the area of a vessel suspected of being diseased, the physician may connect the proximal end of the catheter guide of the imaging guidewire to rotary drive unit 28, by inserting it into mandrel opening 47, and may activate rotary drive unit 28 by pressing push button 49.

Upon pressing of button 49 mandrel 33 is rotated by electric motor 29. Since the proximal end of the catheter guide 24 part of the imaging guidewire is inserted into mandrel 33, the entire guidewire is rotated with the speed of rotation conforming to the speed of rotation of mandrel 33.

The angle of rotation of the imaging guidewire is read electronically be encoder element 22 from encoder disk 26 rotating together with mandrel 33.

Electrical signals from encoder element 22 are transmitted to electronic computer 30 through electrical wires 25 and cable 35.

Electrical pulse signals to activate transducer 14 as well as signals received from transducer 14 are transmitted along the length of the imaging guidewire through metal core 18 and outside metallization shield 20, a set of slip contacts 37, electrical wires 25 and cable 35 to and from electronic computer 30.

Transducer 14 operates on principle of piezoelectricity. When an electric signal is applied across the width of transducer 14, in physical dimension of the PZT transducer, which leads to creation an acoustic wave in the medium surrounding transducer 14.

SUMMARY, RAMIFICATION, AND SCOPE

Accordingly, the reader will see that the ultrasound imaging guidewire of the present invention presents a novel construction and expanded capabilities and offers novel applications of intravascular ultrasound imaging.

Previous inventions and articles have not cited nor anticipated a similar ultrasound imaging guidewire.

The imaging guidewire permits substantial benefits over the existing or anticipated catheters for intraluminal, ultrasound imaging. Imaging guidewire of the present invention permits a physician to monitor plaque in front of the distal tip of angioplasty catheter and thus helps the physician make decision whether to perform angioplasty and gives information about the vessel wall.

Similarly the imaging guidewire of the present invention helps reduce trauma of catheterization by avoiding multiple insertions of catheters, by permitting ultrasound imaging without necessity to insert an imaging catheter.

Furthermore, the present invention has additional advantages in that:

- it allows for a simple construction of an imaging guidewire,
- it allows for an inexpensive method of manufacturing of imaging guidewire and simple attachment of the transducer,
- a small diameter of imaging guidewire and transducer allows for insertion into narrow, and coronary blood vessels,
- construction of imaging guidewire permits its insertion into guidewire lumen of angioplasty catheters, While the above description contains many specificities, the reader should not construct these as limitation on the scope of the invention, but merely as exemplifications on the typical embodiments thereof.

Those skilled in the art will envision many other possible variations are within its scope. For example skilled artisans will readily be able to change the dimensions and shapes of the various embodiments. They will also be able to make many variations on the shape of the transducer assembly, and the method of its attachment to a transducer seat.

They can also vary the materials used for parts of imaging guidewire, such as other metals and plastic or plastic composites and employ different manufacturing techniques for their fabrication.

Similarly they can vary the material used for ultrasonic transducer such as PVDF (polyvinylidiene fluoride), PZT, $BaTiO_3$ (barium titanate), lead metaniobate.

Also the shape of distal guidewire, transducer seat and catheter guide may be changed.

Accordingly the reader is requested to determine the scope of the invention by the appended claims and their legal equivalents, and not by the examples which have been given.

We claim:

1. An imaging/angioplasty apparatus for use in a human or animal vessel, comprising:

an angioplasty catheter having a guidewire lumen surrounded by an inflatable balloon; and an elongated flexible guidewire having a proximal and a distal end, said distal end of said guidewire having a transducer thereon, said guidewire arranged to rotate within said lumen of said catheter, with said inflatable balloon disposed proximally of said transducer on said catheter in an abutting longitudinally-inadvancable manner, to permit steady centralized ultrasonic imaging of plaque within a vessel distally of said angioplasty catheter balloon within that vessel being imaged.

2. The imaging/angioplasty apparatus as recited in claim 1, including a handle with a drive motor attached to said proximal end of said guidewire, to provide rotary motion to said guidewire and said transducer at said distal end of said guidewire.

3. The imaging/angioplasty apparatus as recited in claim 1, including a transducer seat at said distal end of said guidewire for holding said transducer therein as said guidewire rotates within said catheter.

4. The imaging/angioplasty apparatus as recited in claim 1, wherein said guidewire has a metal core for conducting electrical signals to and from said transducer.

5. A method of performing a treating procedure on a human blood vessel comprising the steps of:
   inserting an elongated flexible guidewire having a proximal and a distal end, into a vessel to be treated, said guidewire having an imaging transducer arranged on its distal end;
   pushing a balloon catheter over said proximal end of said guidewire, said guidewire passing through a guidewire lumen of said angioplasty catheter, said catheter having a balloon on its distal end;
   threading said balloon catheter into said vessel over said guidewire only up to said transducer on said distal end of said guidewire to permit a centering relationship between said balloon catheter and said transducer; and
   centering said guidewire in the distal end of said catheter lumen so as to center and permit rotation of said transducer within the walls of a vessel being examined so as to image those walls.

6. The method of performing a treating procedure, as recited in claim 5, including the step of:
   attaching a handle to said proximal end of said guidewire, said handle having a motor arranged therein, to provide rotative empowerment to said guidewire in said catheter.

7. The method of performing a treating procedure, as recited in claim 5, including the step of:
   inflating said balloon to a low first pressure to permit further centering of said transducer with respect to the vessel.

8. The method of performing a treating procedure, as recited in claim 5, including the step of:
   inflating said balloon on said catheter to a second higher pressure to treat the wall of the vessel being imaged.

9. The method of performing a treating procedure, as recited in claim 8, including the step of:
   deflating said balloon on said catheter to permit said transducer and catheter to be moved within the vessel for further treatment thereof.

10. The method of performing a treating procedure, as recited in claim 5, wherein said catheter is an angioplasty catheter.

11. A method of centering an imaging guidewire within a vessel, comprising the steps of:
   inserting an elongated flexible guidewire having a proximal and a distal end within the vessel to be imaged;
   placing a catheter with a guidewire lumen therethrough and a balloon on a distal end thereof, onto the proximal end of said guidewire;
   threading said guidewire through said lumen of said catheter;
   passing said catheter over said guidewire, and up to the distal end of said guidewire in a centralizing relationship therebetween, leaving said distal end of said guidewire exposed within the vessel;
   inflating said balloon to a low first pressure once the distal end of said catheter is adjacent said distal end of said guidewire, so as to centralize said guidewire in the vessel being treated.

12. The method of claim 11, wherein said guidewire has an ultrasonic transducer disposed on said distal end thereof.

13. The method of claim 12, including the step of:
   rotating said ultrasonic transducer and said guidewire once said guidewire has been centralized in the vessel being treated.

14. The method of claim 13, including the step of:
   energizing said transducer so as to generate ultrasonic images of the vessel distal of said balloon at the distal end of said catheter.

15. The method of claim 11, including the step of:
   attaching a handle having a motor therewithin, to said proximal end of said guidewire so as to permit rotation of said guidewire and manipulation of said catheter within the vessel being treated.

16. A method of performing a blood vessel treating procedure comprising the steps of:
   inserting an elongated flexible guidewire having a proximal and a distal end, into a vessel to be treated, said guidewire having an imaging transducer arranged on its distal end;
   pushing a balloon catheter over said proximal end of said guidewire, said guidewire passing through a guidewire lumen of said angioplasty catheter, said catheter having said balloon on its distal end;
   threading said balloon catheter into the vessel over said guidewire, up to said imaging transducer in a self centering relationship therebetween;
   inflating said balloon on said distal end of said catheter to a first light pressure, so as to further centralize said guidewire within said vessel;
   attaching a handle having a motor therewithin, to said proximal end of said guidewire so as to permit rotation of said guidewire and manipulation of said catheter within the vessel being treated;
   rotating said ultrasonic transducer and said guidewire once said guidewire has been centralized in the vessel being treated; and
   energizing said transducer so as to generate ultrasonic images of the vessel at the distal end of said catheter.

17. The method of claim 16, including the step of:
   pressurizing said balloon to a higher plaque treating pressure after said guidewire and transducer have been centralized in the vessel and utilized for vessel analysis.

18. The method of claim 16, including the step of:
   threading said catheter over said guidewire only up to said transducer in a non-overlapping exposed-transducer relationship.

19. The method of claim 16, including the step of:
   mating said proximal end of said guidewire into a receiving mandrel in said handle, in a tight fitting engagement, said receiving mandrel secured to said motor for the transmission of rotary motion therethrough.

20. The method of claim 19, including the step of:
   attaching an encoder on said handle, to permit showing of the angular position of said mandrel thereby.

21. The method of claim 16, including the step of:
   depositing a thin layer of insulation on said guidewire.

22. The method of claim 21, including the step of:
   depositing a thin metallization layer on said guidewire, to permit electronic conduction thereby.

23. The method of claim 16, wherein said treating procedure is an angioplasty procedure, said balloon being expanded to apply pressure against a vessel wall.

24. A method of treating a blood vessel in a human body, comprising the steps of:

inserting a first guidewire having a proximal and a distal end into the vessel being treated said first guidewire having an image generating transducer conductively arranged thereon, adjacent its distal end;

inserting a vessel treating catheter having an inner guidewire lumen, over said inserted first guidewire up to said image generating transducer to permit centering of said transducer with respect to catheter;

imaging the vessel being treated via said first guidewire, to communicate an image to a catheter operator, so as to permit the operator controlling said treating catheter to correctly effect catheter based treatment of the walls of the vessel being treated.

25. The method of claim 24, including the step of:

inspecting said vessel being treated during the treatment procedure by said treating catheter placed over said guidewire, by energization of said transducer thereon.

26. The method of claim 25, wherein said treating catheter has an inflatable treating balloon disposed on the distal end thereof.

27. The method of claim 26, wherein said balloon on said catheter is disposed proximal to said transducer during use on said guidewire.

28. The method of claim 26, including the step of:

rotating said transducer on said guidewire in said vessel to permit imaging of an annular portion of the vessel being treated.

29. The method of claim 28, including the step of:

empowering rotation of said guidewire by connecting a motorized handle to said proximal end of said guidewire.

30. The method of claim 29, including the step of:

encoding rotation of said guidewire in said motorized handle by attaching an encoder disk registered in a pickup sensor therein to said guidewire, to permit status and control of said rotation of said transducer and guidewire, by an operator of said guidewire.

31. The method of claim 26, including the step of:

inflating said balloon on said catheter to effect treatment of the walls of the vessel by said treatment catheter.

32. The method of claim 24, including the step of:

attaching a protective round ball on the distalmost end of said guidewire, to minimize the likelihood of damage to any vessel being treated.

33. An catheter apparatus for use in treating a human or an animal vessel, comprising:

an elongated flexible shaft with a proximal and a distal end, said shaft having a central guidewire lumen arranged to removably receive a guidewire therein, said distal end of said shaft having an inflatable balloon disposed therearound; and an elongated flexible guidewire having a proximal end and a distal end, said distal end of said guidewire having a transducer thereon, said guidewire arranged to rotate centrally and non-eccentrically within said lumen of said catheter, with said transducer centrally rotatably disposed adjacent said inflatable balloon on said catheter, to permit a stable ultrasonic imaging of plaque within a vessel adjacent said balloon on said catheter within that vessel being imaged.

34. The catheter apparatus as recited in claim 33, including a handle with a drive motor attached to said proximal end of said guidewire, to provide rotary motion to said guidewire and said transducer at said distal end of said guidewire, to permit said transducer to rotate within said vessel for imaging thereof.

35. The catheter apparatus as recited in claim 33, including a transducer seat at said distal end of said guidewire for holding said transducer therein, distal of said catheter, as said guidewire rotates within said catheter.

36. The catheter apparatus as recited in claim 35, wherein said guidewire is comprised of a metal conductor for conducting electrical signals to and from said transducer, to permit images generated by said transducer to be viewed by an operator of said apparatus.

* * * * *